US 6,589,183 B2

(12) United States Patent
Yokozeki

(10) Patent No.: US 6,589,183 B2
(45) Date of Patent: Jul. 8, 2003

(54) ARTERIAL-HARDNESS EVALUATING APPARATUS

(75) Inventor: Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/955,191

(22) Filed: Sep. 19, 2001

(65) Prior Publication Data

US 2002/0052552 A1 May 2, 2002

(30) Foreign Application Priority Data

Oct. 30, 2000 (JP) ........................................ 2000-330592

(51) Int. Cl.[7] .................................................. A61B 5/00
(52) U.S. Cl. ........................................ 600/485; 600/500
(58) Field of Search ................................ 600/485, 490, 600/493–6, 500, 503, 504

(56) References Cited

U.S. PATENT DOCUMENTS

| 5,853,371 A | * | 12/1998 | Inukai et al. ................ 600/493 |
| 5,991,654 A | * | 11/1999 | Tumey et al. ................ 600/504 |
| 6,176,832 B1 | * | 1/2001 | Habu et al. .................. 600/485 |
| 6,190,325 B1 | * | 2/2001 | Narimatsu ................... 600/494 |

* cited by examiner

*Primary Examiner*—Robert L Nasser
(74) *Attorney, Agent, or Firm*—Oliff & Berridge, PLC

(57) ABSTRACT

An apparatus for evaluating a degree of hardness of an artery of a living subject, including a blood-flow stopping device which stops a flow of blood through a first portion of the subject, and a blood-amount detecting device which is adapted to be worn on a second portion of the subject that is located on a downstream side of the first portion and which produces a blood-amount signal representing an amount of blood present in the second portion.

6 Claims, 5 Drawing Sheets

ARTERIAL-HARDNESS EVALUATING APPARATUS

BACKGROUND OF THE INVENTION

1. Field of the Invention

The present invention relates to an apparatus for evaluating a degree of hardness of an artery of a living subject.

2. Related Art Statement

The technique of stopping a flow of blood through a portion of a patient for making a diagnosis has been used in only measuring a blood pressure of the patient using an inflatable cuff. When a blood pressure is measured using an inflatable cuff, first, the cuff is wound around a prescribed portion (e.g., an upper arm) of a patient and, after the flow of blood through that portion is stopped by the cuff inflated, the pressing pressure of the cuff is slowly decreased, so that the flow of blood is gradually increased, an oscillatory pressure wave occurring to the cuff is detected and, based on the thus detected pressure wave, the blood pressure is measured. Thus, the cuff-using blood-pressure measuring method does not utilize any physical signals that can be detected on a downstream side of the portion the flow of blood through which is stopped by the cuff.

If the change of amount of blood is observed on the downstream side of the portion around which the cuff is wound, it is possible to find that the amount of blood decreases because of the stopping of flow of blood on the upstream side. The Inventor has found that the tendency of decreasing of the amount of blood is influenced by the degree of hardness of artery of the patient.

SUMMARY OF THE INVENTION

It is therefore an object of the present invention to provide an apparatus which evaluates a degree of hardness of an artery of a living subject based on a tendency of decreasing of amount of blood because of stopping of flow of blood.

The above object has been achieved by the present invention. According to the present invention, there is provided an apparatus for evaluating a degree of hardness of an artery of a living subject, comprising a blood-flow stopping device which stops a flow of blood through a first portion of the subject; and a blood-amount detecting device which is adapted to be worn on a second portion of the subject that is located on a downstream side of the first portion and which produces a blood-amount signal representing an amount of blood present in the second portion.

According to this invention, when the flow of blood in the portion of the subject is stopped by the blood-flow stopping device, the magnitude of the blood-amount signal produced by the blood-amount detecting device worn on the downstream side of the portion decreases. Since the mode of decreasing of the magnitude of the blood-amount signal changes with the degree of hardness of artery of the subject, the arterial hardness can be evaluated based on the blood-amount signal.

Preferably, the evaluating apparatus further comprises an arterial-hardness determining means for determining the degree of hardness of artery of the subject based on a monotonously decreasing curve of the blood-amount signal produced by the blood-amount detecting device in a state in which the flow of blood through the first portion of the subject is stopped by the blood-flow stopping device.

According to this feature, the arterial-hardness determining means quantitatively determines the degree of hardness of artery of the subject based on the blood-amount signal produced by the blood-amount detecting device.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
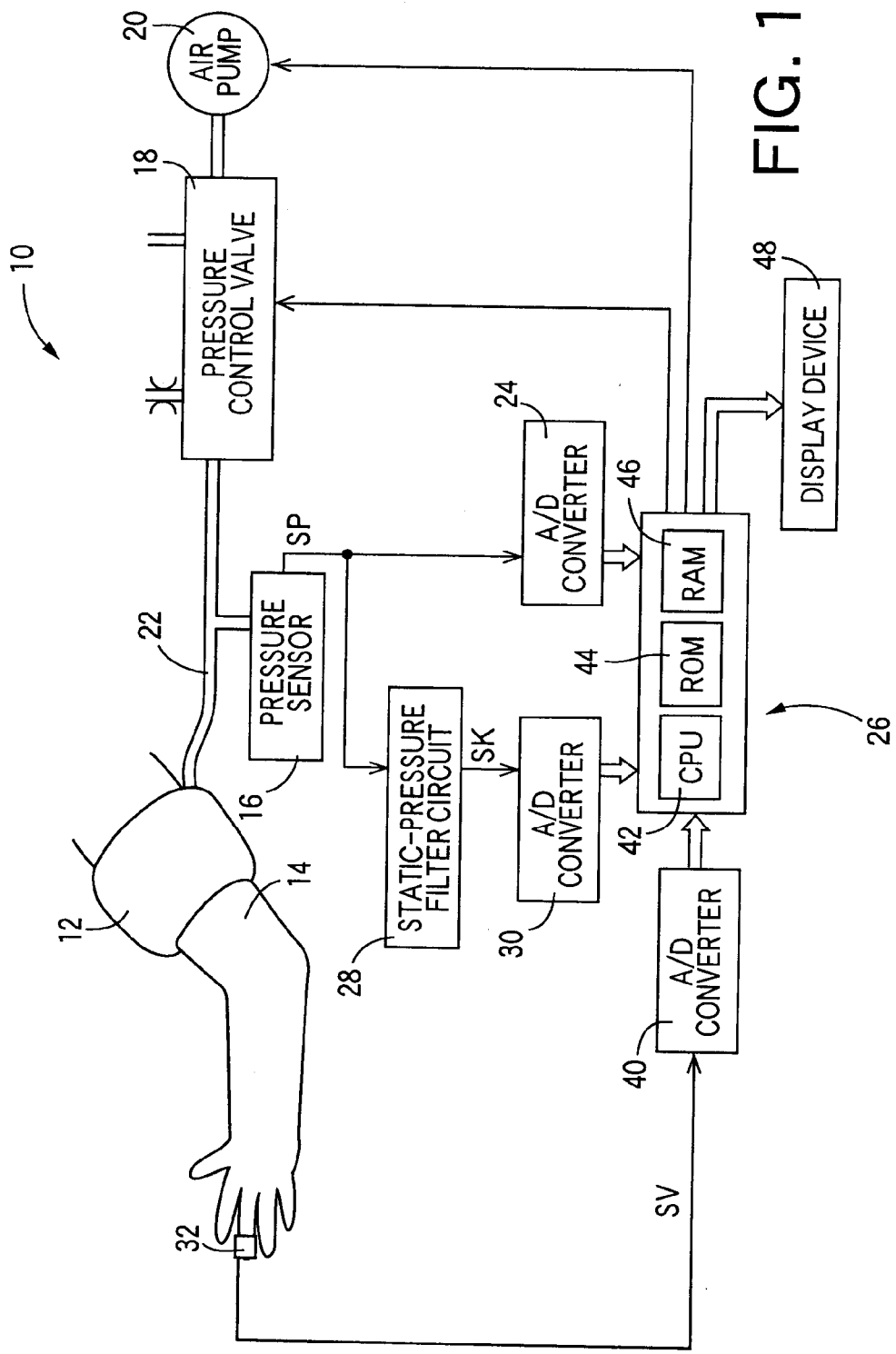
FIG. 1 is a diagrammatic view for explaining a construction of an arterial-hardness evaluating apparatus to which the present invention is applied.

Hereinafter, there will be described an embodiment of the present invention in detail by reference to the accompanying drawings. FIG. 1 shows a diagrammatic view for explaining a construction of an arterial-hardness evaluating apparatus 10 to which the present invention is applied.

In FIG. 1, the arterial-hardness evaluating apparatus 10 includes a cuff 12 which has a belt-like cloth bag and a rubber bag accommodated in the cloth bag and which is adapted to be wound around, e.g., a right upper arm 12 of a patient as a living subject. The cuff 12 is connected to a pressure sensor 16, a pressure control valve 18, and an air pump 20 via a piping 22. The pressure control valve 18 is selectively placed in a pressure-supply position in which the control valve 18 permits a pressurized air to be supplied from the air pump 20 to the cuff 12, a pressure-keep position in which the control valve 18 inhibits the pressurized air from being discharged from the cuff 12 and thereby keeps the air pressure in the cuff 12, and a quick-deflation position in which the control valve 18 permits the pressurized air to be quickly discharged from the cuff 12. When the cuff 12 is supplied with the pressurized air from the air pump 20 and the pressing pressure (i.e., air pressure) of the cuff 12 is increased up to a prescribed value, the cuff 12 stops flow of blood through the upper arm 14 around which the cuff 12 is wound. Thus, the cuff 12 and the air pump 20 cooperate with each other to provide a blood-flow stopping device.

The pressure sensor 16 detects the air pressure in the cuff 10, and supplies a pressure signal SP representing the detected pressure, to a control device 26 via an A/D (analog-to-digital) converter 24, and additionally to a static-pressure filter circuit 28. The static-pressure filter circuit 28 includes a low-pass filter and extracts, from the pressure signal SP, a static-pressure component $P_C$ contained in the signal SP, i.e., a cuff-pressure signal SK representing the static cuff pressure $P_C$. The cuff-pressure signal SK is supplied to the control device 26 via an A/D converter 30.

Figure 2:
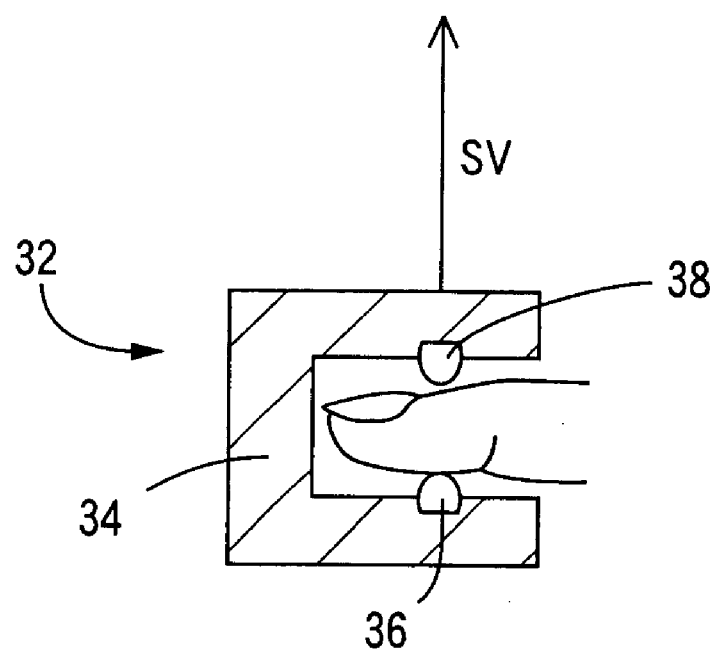
FIG. 2 is a cross section of a blood-amount detecting device as part of the arterial-hardness evaluating apparatus of FIG. 1.

The evaluating apparatus 10 further includes a blood-amount detecting device 32 which is adapted to be worn on an end portion of a finger of the subject that is located on a downstream side of the upper arm 14 around which the cuff 12 is wound, so that the detecting device 32 detects an amount of blood present in peripheral blood vessels of the finger. The blood amount detecting device 32 has the same construction as that of a transmission-type photoelectric-pulse-wave detecting device which is used to detect a photoelectric pulse wave of a living person. FIG. 2 shows a cross section of the detecting device 32, which includes a housing 34 which can accommodate the end portion of the finger; a light emitting element 36, as a light source, which emits, toward a skin of the finger, a red or infrared light having a frequency in a frequency range that is reflected by hemoglobin, preferably, having a frequency (e.g., 660 nm) that is influenced by degree of blood oxygen saturation; and a light receiving element 38 which is supported by the housing 34 such that the light receiving element 38 is opposed to the light emitting element 36, and which receives the light transmitted through the end portion of the finger and produces a blood-amount signal SV representing an amount of blood present in peripheral capillaries of the finger. The blood-amount signal SV produced by the blood-amount detecting device 32 is supplied to the control device 26 via an A/D converter 40.

The control device 26 is provided by a so-called microcomputer including a central processing unit (CPU) 42, a read only memory (ROM) 44, a random access memory (RAM) 46, and an input-and-output (I/O) port, not shown. The CPU 42 processes signals according to the control programs pre-stored in the ROM 44 by utilizing the temporary-storage function of the RAM 46, and supplies drive signals via the I/O port to respective drive circuits, not shown, associated with the pressure control valve 18 and the air pump 20 so as to change the pressure in the cuff 12 and determine a degree of hardness of an artery of the patient based on the blood-amount signal SV supplied from the blood-mount detecting device 32. In addition, the CPU 42 operates a display device 48 to display the thus determined arterial hardness. The display device 48 may include a cathode ray tube (CRT).

Figure 3:
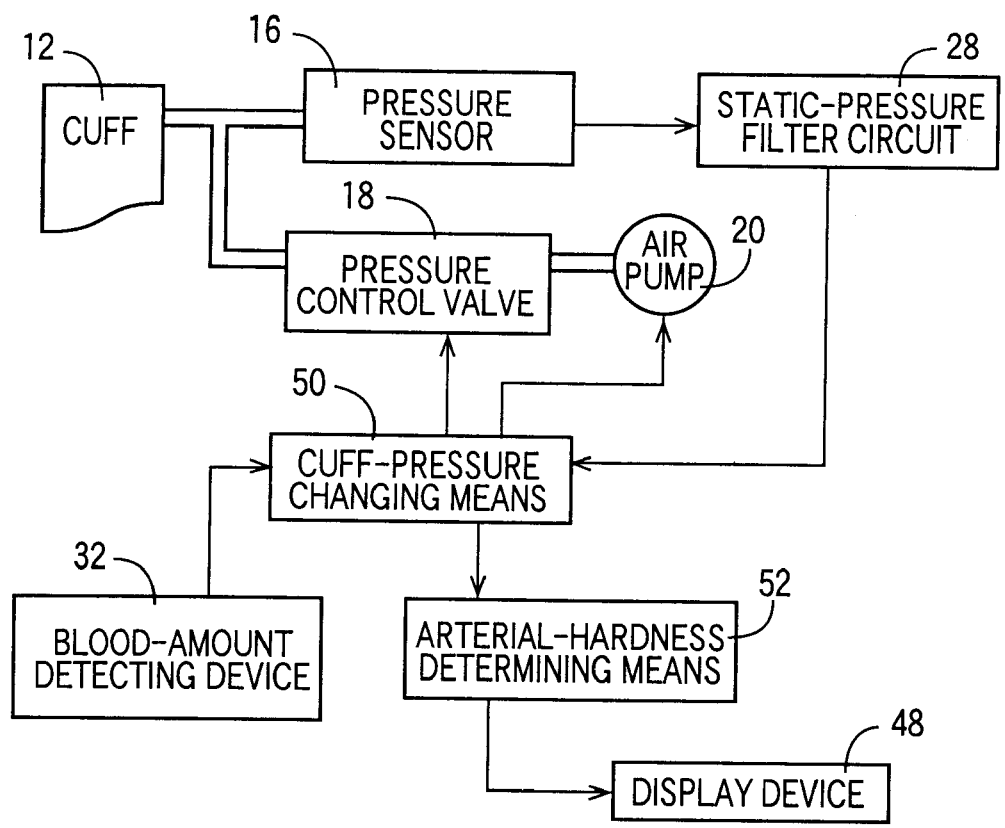
FIG. 3 is a block diagram for explaining essential functions of a control device of the arterial-hardness evaluating apparatus of FIG. 1.

FIG. 3 is a block diagram for explaining essential functions of the control device 26. In the figure, a cuff-pressure changing means 50 operates the pressure control valve 18 and the air pump 20, recognizes the cuff pressure $P_C$ based on the cuff-pressure signal SK supplied from the static-pressure filter circuit 28, quickly increases the cuff pressure $P_C$ up to a prescribed target pressure $P_M$ (e.g., 180 mmHg) to stop the flow of blood through the upper arm 14 around which the cuff 12 is wound, and keeps the cuff pressure $P_C$ for a prescribed pressure-keep time $T_1$. This time $T_1$ is experimentally determined, in advance, as a time needed to detect a blood-amount signal SV needed to determine a degree of hardness of an artery of the patient, described later.

Figure 4:
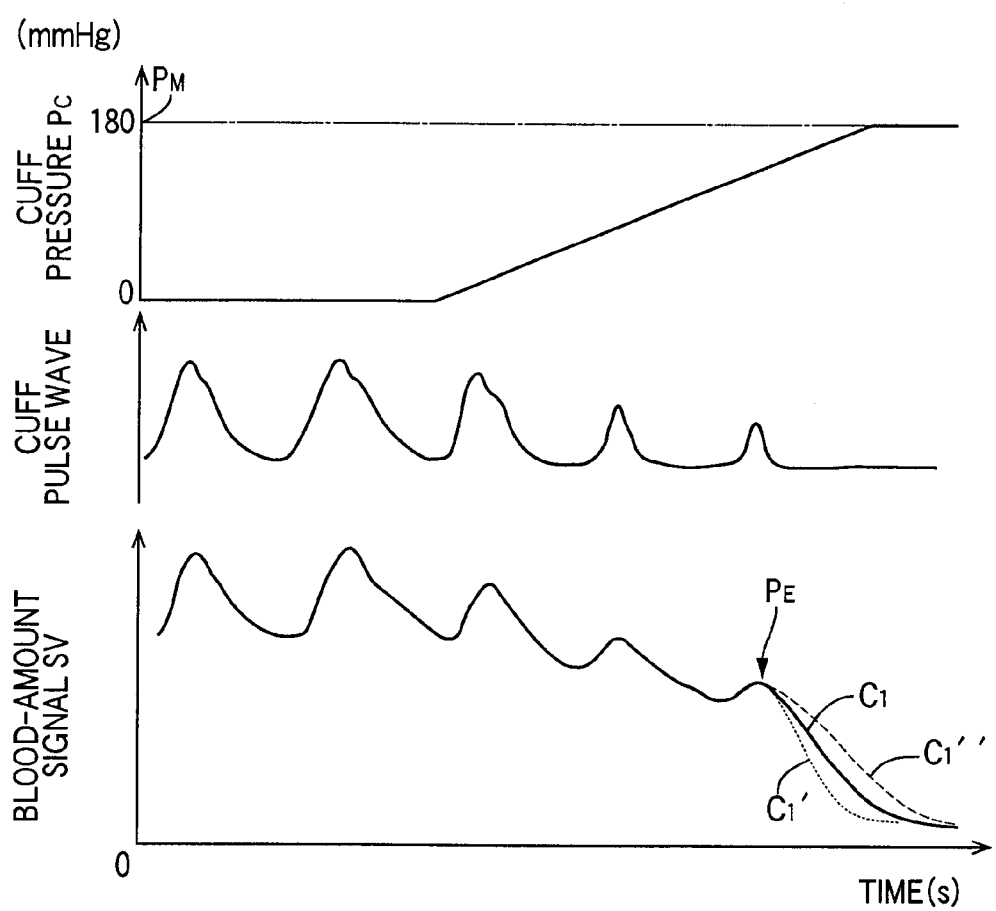
FIG. 4 is a graph showing, along a common time axis, a cuff pressure $P_C$ which is increased by a cuff-pressure changing means shown in FIG. 3, a cuff pulse wave, i.e., an oscillatory component which occurs to a cuff at that time, and a blood-amount signal SV which is produced by the blood-amount detecting device at that time.

FIG. 4 is a graph showing, along a common time axis, the cuff pressure $P_C$ increased by the cuff-pressure changing means 50, a cuff pulse wave, i.e., an oscillatory component which occurs to the cuff 12 at that time, and the blood-amount signal SV produced by the blood-amount detecting device 32 at that time. As shown in FIG. 4, the cuff pulse wave gradually decreases as the cuff pressure $P_C$ increases and, when the cuff pressure $P_C$ reaches the target pressure $P_M$, the cuff pulse wave has already disappeared. That is, when the cuff pressure $P_C$ reaches the target pressure $P_M$, the flow of blood through the upper arm 14 has been completely stopped. In addition, a peripheral-blood-amount curve represented by the blood-amount signal SV produced by the blood-amount detecting device 32 increases and decreases corresponding to the increasing and decreasing of the cuff pulse wave, and gradually decreases as a whole, during an initial period of increasing of the cuff pressure $P_C$. After the flow of blood through the upper arm 14 is completely stopped, the blood-amount signal SV monotonously decreases, indicating a decreasing curve $C_1$.

An arterial-hardness determining means 52 determines a degree of hardness of an artery of the patient based on the decreasing curve $C_1$ of the blood-amount signal SV produced by the blood-amount detecting device 32 in the state in which the flow of blood in the upper arm 14 is stopped by the cuff 12. In addition, the determining means 52 operates the display device 48 to display the thus determined arterial hardness. The tendency of decreasing of the curve $C_1$ is influenced by the hardness of artery. If the arteries are hard, the decreasing curve $C_1$ decreases down to a certain value in a relatively short time, as indicated at $C_1'$ and, if the arteries are flexible, the curve $C_1$ decreases down to a certain value in a relatively long time, as indicated at $C_1''$.

Therefore, the arterial-hardness determining means 52 determines, as a degree of hardness of artery of the patient, a relative value (hereinafter, referred to as a blood-amount relative value r) of a magnitude of the blood-amount signal SV, i.e., the decreasing curve $C_1$, detected a prescribed time (e.g., from 1 to 2 seconds) after a time of detection of a prescribed reference point of the signal SV, relative to a magnitude of the reference point of the signal SV; a decreasing time t (sec) which is needed for the blood-amount signal SV to decrease from the magnitude of the reference point by a prescribed proportion of the magnitude; or a time constant $\tau$ (sec) of the curve $C_1$ starting with the reference point. The reference point of the blood-amount detecting signal SV may be the last one $P_E$ of successive peaks occurring to the blood-amount curve represented by the signal SV, or a point of the signal SV that corresponds to the time when the cuff pressure $P_C$ reaches the target pressure $P_M$. The relative value t may be a ratio of the first magnitude of the signal SV detected the prescribed time after the time of detection of the reference point of the signal SV, relative to the second magnitude of the reference point of the signal SV, a difference value obtained by subtracting the first magnitude from the second magnitude, or a ratio of the difference value to the second magnitude. Otherwise, the arterial hardness may be determined as an evaluation value which is obtained from the blood-amount relative value r, the decreasing time t, or the time constant $\tau$ according to a prescribed relationship between evaluation value and parameter r, t, or $\tau$.

The reason why the mode of decreasing of the curve $C_1$ is influenced by the arterial hardness has not been fully elucidated. However, it can be speculated as follows: When a flow of blood through a portion of a living person is stopped, a flow of blood on a downstream side of that portion, however, is not simultaneously stopped, and a small amount of blood flow remains because of the pressure difference between arteries and veins. If the arteries are normal, i.e., sufficiently soft, those vessels radially expand and contract, thereby keeping the arterial pressure to some extent. Thus, a considerably long time is needed for the pressure difference to decrease to zero. Therefore, in a peripheral portion, e.g., an end portion of a finger, a flow of blood slowly decreases because of the expansion and contraction of arteries located between the peripheral portion and the portion the flow of blood through which is stopped. On the other hand, if the arteries are hard, those vessels radially expand and contract, with difficulty, so that in a considerably short time duration, the pressure difference between the arteries and the veins decreases down to zero and accordingly the flow of blood in the peripheral portion decreases in a considerably short time duration.

Next, there will be described the operation of the control device 26, by reference to the flow chart shown in FIG. 5. The control routine represented by the flow chart is started when a start button, not shown, is operated by an operator, e.g., medical staff.

Figure 5:
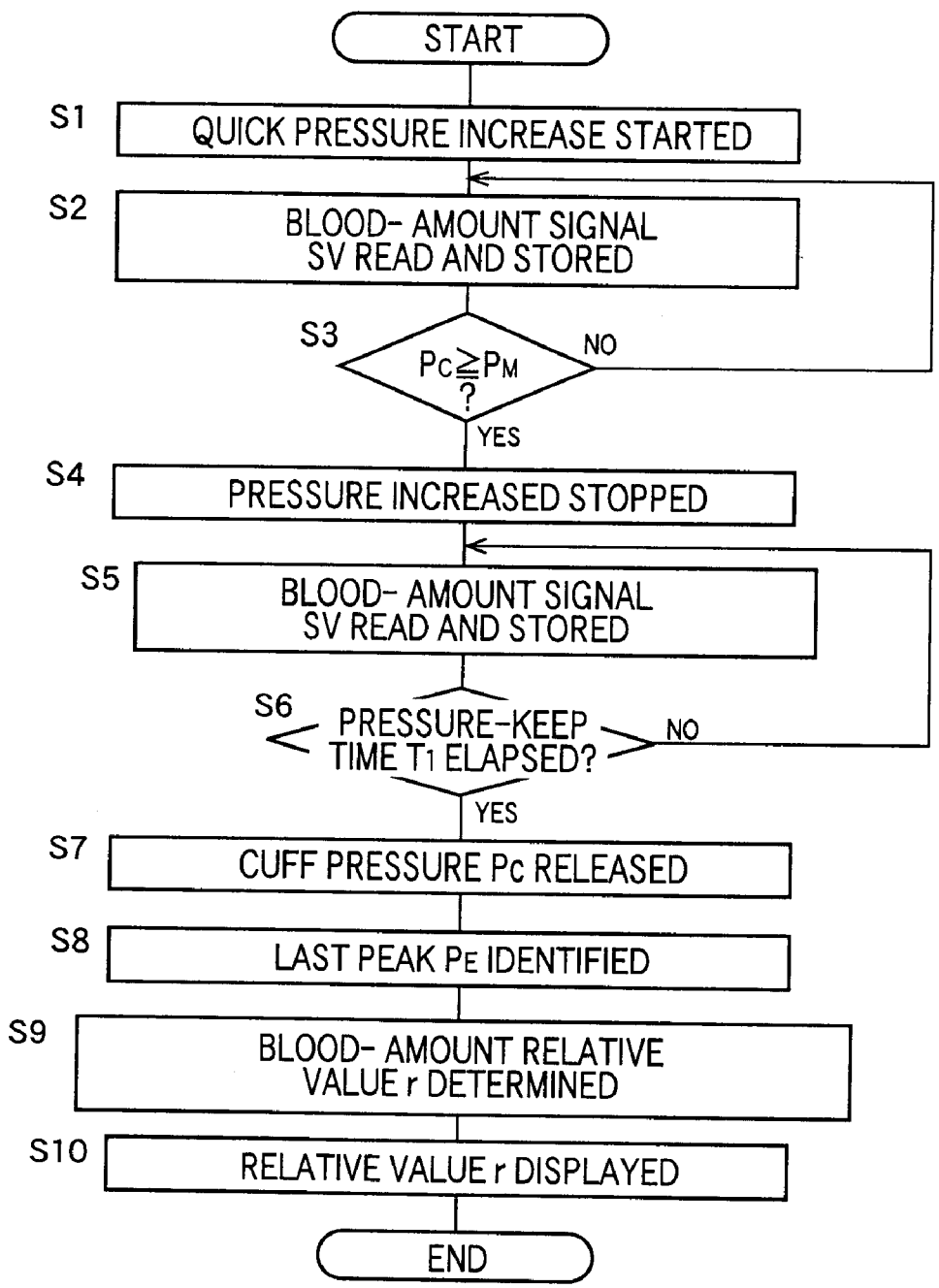
FIG. 5 is a flow chart representing a control program according to which the control device shown in FIG. 1 is operated.

In FIG. 5, first, at Step S1 (hereinafter, "Step" is omitted, if appropriate), the control device 26 switches the pressure control valve 18 to its pressure-supply position and operates the air pump 20, so that the cuff pressure $P_C$ is quickly increased at a rate of 70 mmHg/sec.

Then, at S2, the control device 26 reads in a prescribed number of data points of the blood-amount signal SV supplied from the blood-amount detecting device 32, and stores the thus read data points of the signal SV in a prescribed memory area of the RAM 46.

At S3, the control device 26 judges whether the cuff pressure $P_C$ has reaches the prescribed target pressure $P_M$, i.e., 180 mmHg. Steps S2 and S3 are repeated until a positive judgment is made at S3, so that the quick inflation of the cuff 12 is continued and the reading of data points of the blood-amount signal SV is continued.

Meanwhile, if a positive judgment is made at S3, the control proceeds with S4 to stop the air pump 20 and switch the pressure control valve 18 to its pressure-keep position, so that the cuff pressure $P_C$ is kept at the target pressure $P_M$.

Then, at S5, the control device 26 reads in, like at S2, a prescribed number of data points of the blood-amount signal SV supplied from the blood-amount detecting device 32, and stores the thus read data points in another prescribed memory area of the RAM 46. S5 is followed by S6 to judge whether the prescribed pressure-keep time $T_1$, e.g., 2 seconds, has elapsed after the pressure control valve 18 is switched to the pressure-keep position at S4.

If a negative judgment is made at S6, Steps S5 and S6 are repeated until a positive judgment is made at S6, so that the cuff pressure $P_C$ is kept at the target pressure $P_M$ and the reading of data points of the blood-amount signal SV is continued. Meanwhile, if a positive judgment is made at S6, the control goes to S7 to switch the pressure control valve 18 to its quick-deflation position, so that the cuff pressure $P_C$ is quickly released. In the present flow chart, Steps S1, S3, S4, S6, and S7 correspond to the cuff-pressure changing means 50.

Then, the control goes to S8 and S9 corresponding to the arterial-hardness determining means 52. First, at S8, the control device 26 identifies, on a blood-amount curve represented by the data points of the blood-amount signal SV stored at S2 and S5, the last one $P_E$ of successive peaks or maximal points of the blood-amount curve, and determines a magnitude of the identified last peak $P_E$ as a magnitude of a start point of the decreasing curve $C_1$ of the blood-amount curve. Then, at S9, the control device 26 determines a magnitude of the blood-amount signal SV, i.e., the decreasing curve $C_1$, detected two seconds after a time of detection of the last peak $P_E$ determined at S8, and determines, as a degree of hardness of an artery of the patient, a blood-amount relative value r of the two-second-after magnitude of the curve $C_1$ relative to the magnitude of the start point of the curve $C_1$.

Finally, at S10, the control device 26 operates the display device 48 to display the blood-amount relative value r determined at S9.

It emerges from the foregoing description of the illustrated embodiment that when the flow of blood in the upper arm 14 is stopped by the cuff 12, the magnitude of the blood-amount signal SV produced by the blood-amount detecting device 32 worn on the downstream side of the upper arm 14 decreases. Since the mode of decreasing of the magnitude of the blood-amount signal SV changes with the degree of hardness of artery of the patient, the arterial hardness can be evaluated based on the blood-amount signal SV.

In addition, in the illustrated embodiment, the arterial-hardness determining means 52 (S8 and S9) determines the arterial hardness based on the decreasing curve $C_1$ of the blood-amount signal SV produced by the blood-amount detecting device 32. Therefore, the arterial hardness can be evaluated on a quantitative basis.

While the present invention has been described in its preferred embodiment by reference to the drawings, it is to be understood that the invention may otherwise be embodied.

For example, in the illustrated arterial-hardness evaluating apparatus 10, the cuff 12 is adapted to be wound around the upper arm 14. However, it is possible to employ an inflatable cuff which is adapted to be wound around a wrist, a femur, or an ankle.

In addition, in the illustrated arterial-hardness evaluating apparatus 10, the cuff 12 and the air pump 20 cooperate with each other to function as the blood-flow stopping device. However, the blood-flow stopping device may employ, in place of the cuff 12, a pressing device which is adapted to be worn on a prescribed portion of a living person, is connected to the air pump 20, and presses a skin right above a prescribed artery (e.g., a radial artery). Alternatively, the blood-flow stopping device may be one which includes a band that is generally cylindrically curved so as to be wound around a prescribed portion of a living person, and a wind-up device that winds up the band around the portion of the person with a prescribed force.

In addition, in the illustrated arterial-hardness evaluating apparatus 10, the transmission-type blood-amount detecting device 32 is adapted to be worn on the end portion of finger of the patient. However, the blood-amount detecting device may be provided by a reflection-type photoelectric-pulse-wave detecting device and, in this case, the detecting device may be adapted to be worn on the back or wrist of hand.

It is to be understood that the present invention may be embodied with other changes, improvements, and modifications that may occur to a person skilled in the art without departing from the spirit and scope of the invention defined in the appended claims.

What is claimed is:

1. An apparatus for evaluating a degree of hardness of an artery of a living subject, comprising:

a blood-flow stopping device which stops a flow of blood through a first portion of the subject;

a blood-amount detecting device which is adapted to be worn on a second portion of the subject that is located on a downstream side of the first portion and which produces a blood-amount signal representing an amount of blood present in the second portion; and an arterial-hardness determining means for determining the degree of hardness of artery of the subject based on a decreasing curve of the blood-amount signal produced by the blood-amount detecting device in a state in which the flow of blood through the first portion of the subject is stopped by the blood-flow stopping device.

2. An apparatus according to claim 1, wherein the arterial-hardness determining means comprises means for determining the degree of hardness of artery of the subject based on a change of magnitude of the decreasing curve of the blood-amount signal in a predetermined time duration.

3. An apparatus according to claim 1, wherein the arterial-hardness determining means comprises means for determining the degree of hardness of artery of the subject based on a time duration needed for a predetermined amount of change of magnitude of the decreasing curve of the blood-amount signal.

4. An apparatus according to claim 1, wherein the blood-flow stopping device comprises:

an inflatable cuff which is adapted to be worn on the first portion of the subject; and a gas pump which supplies a pressurized gas to the cuff to press the first portion of the subject and thereby stop the flow of blood through the first portion.

5. An apparatus according to claim 1, wherein the blood-amount detecting device comprises:

a light emitter which emits a light toward the second portion of the subject; and a light receiver which receives the light from the second portion and produces the blood-amount signal representing an amount of the light received from the second portion and thereby representing the amount of blood present in the second portion.

6. An apparatus according to claim 1, further comprising a display device which displays the degree of hardness of artery determined by the arterial-hardness determining means.

* * * * *